(12) United States Patent
Nelson

(10) Patent No.: US 8,591,832 B2
(45) Date of Patent: Nov. 26, 2013

(54) MULTI-CHANNEL WELLPLATE FILLING SYSTEM

(75) Inventor: Gary Nelson, Hollis, NH (US)

(73) Assignee: Integra Biosciences Corp., Hudson, NH (US)

( * ) Notice: Subject to any disclaimer, the term of this patent is extended or adjusted under 35 U.S.C. 154(b) by 0 days.

(21) Appl. No.: 13/358,790

(22) Filed: Jan. 26, 2012

(65) Prior Publication Data

US 2012/0195811 A1  Aug. 2, 2012

Related U.S. Application Data

(60) Provisional application No. 61/437,417, filed on Jan. 28, 2011.

(51) Int. Cl.
*B01L 3/02* (2006.01)
*G01N 1/22* (2006.01)
*G01N 21/00* (2006.01)
*G01N 33/00* (2006.01)
*G01N 31/00* (2006.01)

(52) U.S. Cl.
USPC ............. 422/522; 422/509; 422/516; 422/63; 422/519; 422/521; 73/864

(58) Field of Classification Search
USPC ....................................................... 422/522
See application file for complete search history.

(56) References Cited

U.S. PATENT DOCUMENTS

| | | | |
|---|---|---|---|
| 3,327,535 A | 6/1967 | Sequeira | |
| 3,802,782 A | 4/1974 | Natelson | |
| 4,102,368 A * | 7/1978 | Marfurt et al. | 141/250 |
| 4,200,607 A * | 4/1980 | Suzuki | 422/64 |
| 4,262,711 A | 4/1981 | Anderson | |
| 4,493,896 A | 1/1985 | La Motte, III et al. | |
| 4,681,742 A | 7/1987 | Johnson et al. | |
| 5,192,505 A * | 3/1993 | Sakagami | 422/64 |
| 5,736,105 A * | 4/1998 | Astle | 422/509 |
| 6,148,878 A | 11/2000 | Ganz et al. | |
| 6,589,483 B1 * | 7/2003 | Maeda | 422/525 |
| 7,662,343 B2 | 2/2010 | Mathus et al. | |

(Continued)

FOREIGN PATENT DOCUMENTS

EP   0 210 014   1/1987

OTHER PUBLICATIONS

Jencons-PLS, Microplate Equipment Brochure, pp. 619-653, at least as early as Jan. 26, 2011—Admitted Prior Art.

(Continued)

*Primary Examiner* — Jill Warden
*Assistant Examiner* — Brittany Fisher
(74) *Attorney, Agent, or Firm* — Andrus, Sceales, Starke & Sawall, LLP

(57) ABSTRACT

A multi-channel wellplate filling system has a peristaltic pump for pumping fluid through multiple flexible tubes. The system also includes multiple pipette tip mounting shafts arranged in a linear array and in fluid communication with a respective flexible tube of the tubing set. Disposable pipette tips are mounted on the pipette tip mounting shafts. A controller operates the peristaltic pump in reverse and forward directions respectively in order to aspirate liquid into disposable pipette tips mounted on the pipette tip mounting shafts and dispense liquid in a metered amount from the disposable pipette tips into a wellplate positioned on a wellplate platform in the system. The system can also be converted into a wellplate wash station.

27 Claims, 10 Drawing Sheets

(56) References Cited

U.S. PATENT DOCUMENTS

| | | | |
|---|---|---|---|
| 7,662,344 | B2 | 2/2010 | Mathus et al. |
| 7,811,522 | B2 * | 10/2010 | Mathus et al. ............... 422/400 |
| 2002/0006359 | A1 | 1/2002 | Mathus et al. |
| 2002/0044894 | A1 * | 4/2002 | Lebl et al. ...................... 422/99 |
| 2002/0104389 | A1 | 8/2002 | Hovey |
| 2002/0174884 | A1 * | 11/2002 | Certa et al. ................ 134/22.18 |
| 2003/0230488 | A1 * | 12/2003 | Lee et al. ....................... 204/453 |
| 2004/0200509 | A1 | 10/2004 | Felder et al. |
| 2005/0079106 | A1 | 4/2005 | Baker et al. |
| 2005/0180883 | A1 | 8/2005 | Maeda et al. |
| 2006/0002824 | A1 * | 1/2006 | Chang et al. ................ 422/100 |
| 2006/0040398 | A1 * | 2/2006 | Schulz et al. ................ 436/43 |
| 2007/0105214 | A1 * | 5/2007 | Micklash et al. ........... 435/306.1 |
| 2007/0292308 | A1 * | 12/2007 | Horan et al. ................... 422/63 |
| 2008/0038129 | A1 | 2/2008 | Higuichi |
| 2011/0076205 | A1 | 3/2011 | Kelly et al. |

OTHER PUBLICATIONS

FluidX, Automated reagent dispensor for 96, 384 and 1536-23II microplates, Xrd-384, 2009 FluidX Ltd. (2 pgs.).

WellMate Setup Instructions for 6, 12, 24, & 48 well Plate Dispensing, www.matrixtechcorp.com/downloads/WellMatesetup, 5 pgs., visited May 10, 2012.

Integra Dose It Dispensing Made Easy, Integra Biosciences Corp., 171099 V02 Flyer Dose It, www.integra-biosciences.com/sites/dose it, 4 pgs., visited May 10, 2012.

Thermo Scientific Matrix WellMate and Microplate Stacker, P-2008-0011, 2008 Thermo Fisher Scientific, 2 pgs.

International Preliminary Report on Patentability, PCT/US2012022683, date of mailing Aug. 8, 2013.

\* cited by examiner

MULTI-CHANNEL WELLPLATE FILLING SYSTEM

FIELD OF THE INVENTION

The invention pertains to multi-channel wellplate filling systems.

BACKGROUND OF THE INVENTION

Programmable multi-channel wellplate filling stations are widely used by laboratory workers to fill wellplates with liquid reagent. A 96-well plate includes eight (8) rows and twelve (12) columns of wells each spaced apart at a nine (9) millimeter centerline to centerline distance. A 384-well plate include sixteen (16) rows and twenty four (24) columns of wells each spaced apart at a centerline to centerline distance of 4.5 millimeters. Most available multi-channel wellplate filling systems have either 8 channels or 16 channels for simultaneously filling 8 or 16 wells in a column on the wellplate. Normally, an 8-channel filling system is used to fill 96-well plates, whereas either an 8-channel or a 16-channel filling system is used to fill 384-well plates. Some 8-channel or 16-channel systems can be used to fill 1536-well plates.

There are several types of multi-channel wellplate filling stations. One type uses a peristaltic pump and tubing set to transfer fluid from a reagent bottle to wells on a wellplate. A typical 8-channel system has a linear array of filling nozzles located on a removable cartridge to which a tubing set having eight (8) flexible tubes is connected such that the tubes are in fluid communication with the filling nozzles. The tubing set is mounted through a peristaltic pump. The open ends of the flexible tubes are placed within a reagent bottle and the peristaltic pump is controlled to pump liquid reagent through the filling nozzles into one column of wells on a wellplate. The position of a wellplate platform on the filling station is indexed to the position of the next column on the wellplate under the array of filling nozzles prior to filling the next column of wells with reagent form the bottle.

The tubing set is calibrated by pre-stretching a portion of each respective flexible tube between pump mounting heads. The peristaltic pump operates on the pre-stretched portions of the flexible tubes to transfer metered amounts of liquid as directed by the controller into wells on a wellplate in the filling station. Before operating the filling station, it is necessary to prime the tubing set which entails placing the open ends of the flexible tube in the reagent bottle and running the peristaltic pump in order to fill each of the flexible tubes in the tubing set. Normally, a waste trough is provided next to the wellplate platform in order to dispense waste reagent. Waste can occur during the priming step or during other steps of the filling process. Once the pre-stretched flexible tubes are fully primed, it is also common to run the pump to dispense the first dispense into the waste trough. Discarding the first dispense is known to improve the accuracy of such filling systems. Then, the controller then operates the drive mechanisms and the peristaltic pump to transfer metered amounts of liquid reagent into the column of wells positioned underneath the array of filling nozzles and reposition the wellplate under the array of filling nozzles. After the filling operation is complete, it is common for the system to dispense the reagent remaining in the flexible tubes into the waste trough.

One of the drawbacks of such a flow-through system is that the flexible tubes of the tubing set require a relatively large residual volume in order for the system to operate. Such flow-through systems are therefore particularly ineffective when the laboratory worker has only a small amount of liquid reagent or in circumstances where the liquid reagent is a valuable commodity.

SUMMARY OF THE INVENTION

In one aspect, the invention is an improvement pertaining to multi-channel wellplate filling systems that substantially eliminates the need for residual reagent volume in the flexible tubes of a tubing set for a peristaltic pump. More specifically, a multi-channel wellplate filling station constructed in accordance with the invention includes a repositionable wellplate platform for holding a multi-well plate. A motorized X-axis drive mechanism repositions the wellplate platform horizontally along an X-axis. The filling system also includes a peristaltic pump and a tubing set including multiple flexible tubes. In accordance with the invention, the filling system also includes multiple pipette tip mounting shafts arranged in a linear array extending along an axis (i.e. Y-axis) that is perpendicular to the axis (i.e. X-axis) along which the position of the wellplate platform is indexed. Each of the pipette tip mounting shafts is in fluid communication with one of the respective flexible tubes of the tubing set. The pipette tip mounting shafts are adapted to receive a disposable pipette tip of the kind that is used in the art on hand held pipettors or on heads for automated liquid handling systems. The system also includes a controller that has a user interface to program the multi-channel wellplate filling system to aspirate liquid into the disposable pipette tips mounted on the mounting shafts and then dispense the liquid from the disposable pipette tips into wells in a multi-wellplate on the repositionable wellplate platform.

In an exemplary configuration, the array of pipette tip mounting shafts are located at a fixed location along the X-axis, and the system includes a motorized drive to lower and lift the array of pipette tip mounting shafts at this fixed location along the X-axis. Desirably, a reagent reservoir is located at this location below the array of pipette tip mounting shafts. To begin operation, disposable pipette tips are mounted onto the array of tip mounting shafts. Then as mentioned, the controller directs the system to move the disposable pipette tips into liquid reagent contained within the reagent reservoir, and drives the peristaltic pump in a reverse direction in order to aspirate liquid into the disposable pipette tips via air displacement. The pipette tips are then positioned over a respective column of wells and the controller directs the peristaltic pump to move in the forward direction in a controlled manner to dispense a metered amount of liquid from the disposable pipette tips into the respective wells in the wellplate on the platform. In an 8-channel system, the disposable pipette tips are preferably capable of aspirating and dispensing up to 300 ml. In a 16-channel system, the disposable pipette tips are preferably capable of aspirating and dispensing up to 125 ml. Those skilled in the art will appreciate that the invention as described avoids the need for filling the flexible tubes of the tube set with liquid reagent in order to prime the system, and that it also avoids waste reagent in the flexible tubes after filling has been completed. Another advantage of the invention is the ability of the system to aspirate reagent from a column of wells in a well plate, and dispense the reagent in another column of the well plate thereby enabling the system to conduct serial dilutions.

It is desirable that the tubing set include a nozzle cartridge having a plurality of interfacing nozzles similar to filling nozzles used in the prior art as well as the flexible tubes connected to the cartridge and the interfacing nozzles. It is further desired that the array of pipette tip mounting shafts be mounted on a mounting shaft cartridge that is attachable to the nozzle cartridge. Preferably, the mounting shaft cartridge can be easily removed from the instrument to enable disposable pipette tips to be loaded and ejected with the cartridge off the instrument. A latching mechanism attaches the pipette tip mounting shaft cartridge to the interfacing nozzle cartridge such that the sealing rings or a gasket are compressed to provide a fluid tight seal when the cartridges are latched together. It is further preferred that the tip mounting shaft cartridge includes a stripping mechanism in order to mechanically strip disposable pipette tips from the mounting shafts on the cartridge. The system can be operated in a flow-through manner if desired by detaching the mounting shaft cartridge.

In a preferred embodiment, the wellplate filling system has a motorized Z-axis drive mechanism to drive the linear array of pipette mounting in a vertical up or down direction. It is possible however within the scope of the invention to move the linear array of pipette tip mounting shafts vertically up and down by a manual mechanism. It is also preferred that the wellplate filling system include a motorized Y-axis drive mechanism that moves the linear array of pipette tip mounting shafts horizontally along a Y-axis in order to reposition the pipette tip mounting shafts in a direction perpendicular to the X-axis in which the wellplate platform is indexed, such as for repositioning the pipette tip mounting shafts to different wells located in the same X-axis location.

The system also desirably contains software to direct the drive mechanisms to touch-off drops of liquid from the end of the respective pipette tips into an array of wells on wellplate after dispensing liquid into the array of wells. This feature requires coordination between the Z-axis drive mechanism which vertically lifts and lowers the pipette tips and the X-axis drive mechanism that indexes the position of the wellplate platform.

The centerline to centerline distance of the pipette tip mounting shafts is preferably 9 mm for an 8-channel system. An 8-channel system with 9 mm centerline to centerline spacing between the mounting shafts can be configured with a Y-axis motor drive (or manual Y-axis shift) to shift the pipette tip mounting shafts in order to fill all 16 wells in a column on a 384 wellplate. Alternatively, for filling 384 wellplates, a 16-channel system with 4.5 mm centerline to centerline distance can be used. Of course, 1536 wellplates can be filled by shifting the array of pipette tip mounting shafts in either an 8-channel or 16-channel system along a Y-axis.

In another aspect of the invention, a multi-channel wellplate filling system generally as described above is capable of being converted into a wellplate washing station. In this regard, the wellplate filling station includes a plate washing head having multiple pairs of needles comprising a wash needle and a vacuum needle. The vacuum needle in each pair desirably extends further down than the wash needle. The multiple pairs of needles are arranged in a linear array, such as a linear array of 8 pairs of needles for an 8-channel system. A washing tube set having multiple flexible tubes is in fluid communication with the wash needles on the plate washing head. The peristaltic pump pumps washing fluid through the flexible tubes on the plate washing head. A vacuum source is connected to the vacuum needles on the plate washing head as well. In use, the array of needle pairs is lowered into wells on a wellplate on the wellplate platform. The peristaltic pump pumps washing fluid into the respective wells, and control of the X and Y position of the wellplate moves the needle pairs around each well, e.g., with circular relative motion, during which time the vacuum source is activated so that the vacuum needles suck the washing fluid out of the respective wells. The system control then moves the needle pairs to the next set of wells to be filled with washing fluid and vacuumed. The plate washing head preferably includes a manifold having passageways between the vacuum needles and the vacuum source. Thus, the multi-channel wellplate filling system can be conveniently converted into a wash station by replacing a mounting shaft cartridge and tube set with a plate washing head and tube set, supplying washing fluid to the flexible tubes passing through the peristaltic pump and hooking the plate washing head up to a vacuum source. After washing is completed, it will be desirable to rinse the wash station tubing set by pumping rinse fluid through the tubing set. All of these components and functions are desirably controlled by the system electronic control unit.

It should be apparent to those skilled in the art that a multi-channel wellplate filling system as described can be operated in three modes. First, the wellplate filling system can be operated in a flow-through mode wherein the interfacing nozzles on the nozzle cartridge are used directly to fill wells in a wellplate by pumping liquid reagent from a reagent bottle through the entire tube set to the wells in a wellplate positioned on the wellplate platform. Alternatively, a suitable mounting shaft cartridge is attached to the nozzle cartridge to provide an array of pipette tip mounting shafts. In this configuration, the system is operated to aspirate reagent from a reagent reservoir into the respective pipette tips and then dispense metered amounts of reagent into wells on a wellplate positioned on a wellplate platform. As mentioned, this mode of operation is particularly desirable when the liquid reagent is scarce or expensive. The ability to aspirate also enables the systems to aspirate from wells in a well plate placed on the station, which as mentioned enables the system to conduct serial dilutions. Finally, the wellplate filling system can be converted into a plate wash station by attaching the plate wash head, placing the flexible tubing into a bottle of rinsing fluid similar to the flow-through operation, and also hooking the plate wash head up to the vacuum source. Various features and aspects of the invention may be practiced independently.

The system may also include a second peristaltic pump controlled by the system controller. Both ends of the tubing for this second peristaltic pump are placed in a reagent bottle, and the system controller runs the second peristaltic pump in order to mix the liquid in the reagent bottle.

Other features and advantages of the invention may be apparent to those skilled in the art upon reviewing the following drawings and description thereof.

BRIEF DESCRIPTION OF THE DRAWINGS

FIG. 11 also shows a second peristaltic pump controlled by the system for mixing liquid within the reagent bottle.

DETAILED DESCRIPTION OF THE EXEMPLARY EMBODIMENT

Figure 11:
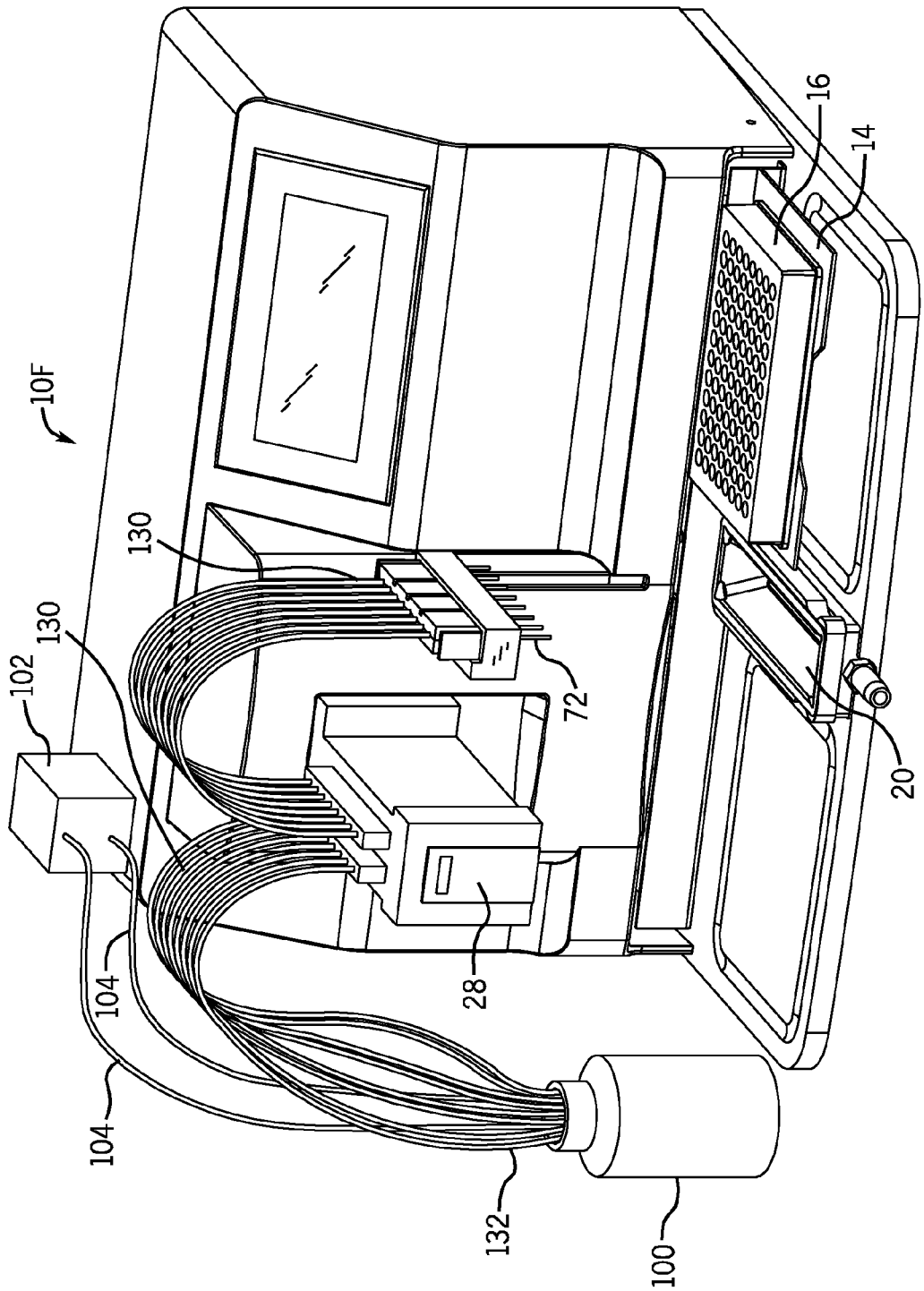
FIG. 11 is a perspective view of the station shown in FIG. 1 set up in flow-through mode with flexible tubing placed directly into a bottle of liquid reagent.
Figure 12:
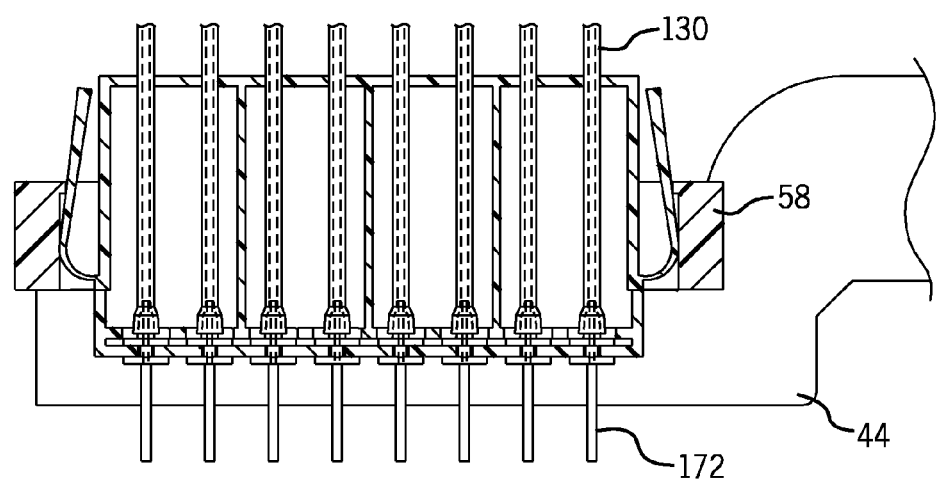
FIG. 12 is a detailed view of a filling nozzle head for the preferred flow-through tube set.
Figure 13:
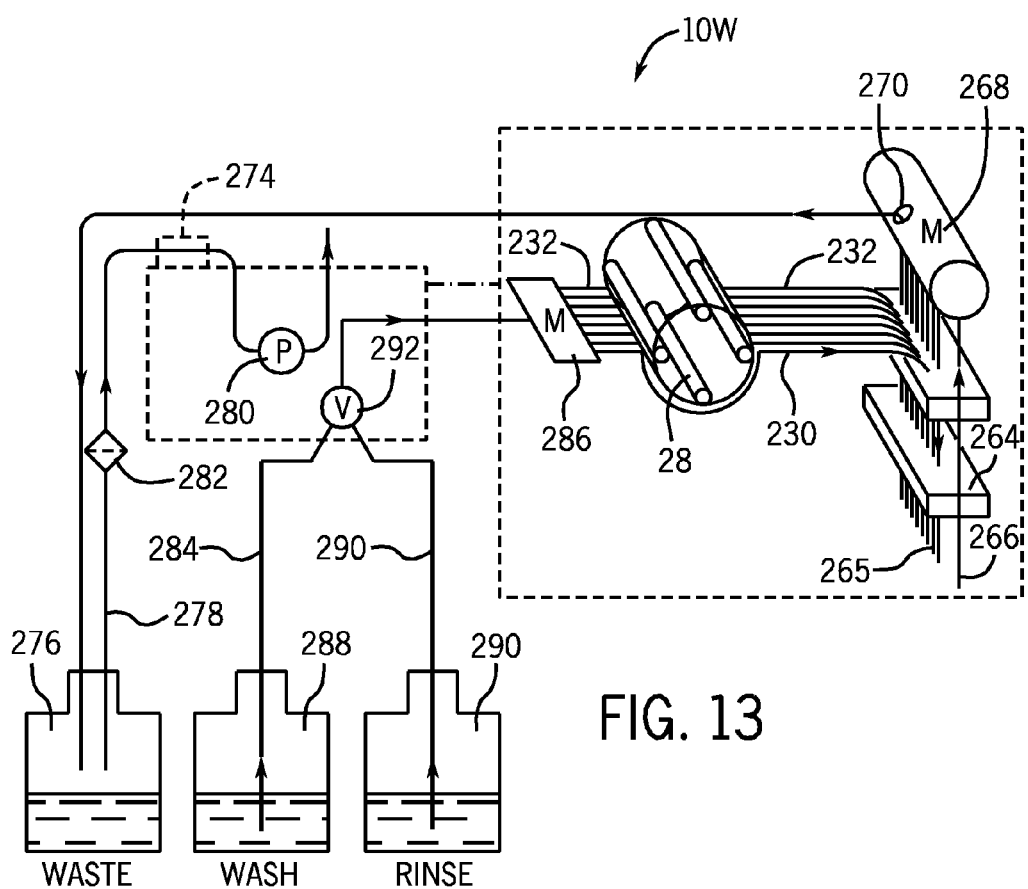
FIG. 13 is a schematic view of the multi-channel wellplate filling station illustrated in previous figures describing its operation after being set up to operate as a wellplate wash station.

A multi-channel wellplate filling system 10 constructed in accordance with an exemplary embodiment of the invention is shown in FIGS. 1-13. FIGS. 1-10 illustrate the system 10 set up to operate with disposable pipette tips 12. FIGS. 11 and 12 illustrate the system 10F in flow-through mode. FIG. 13 shows the system 10W reconfigured as a wellplate wash station.

Figure 1:
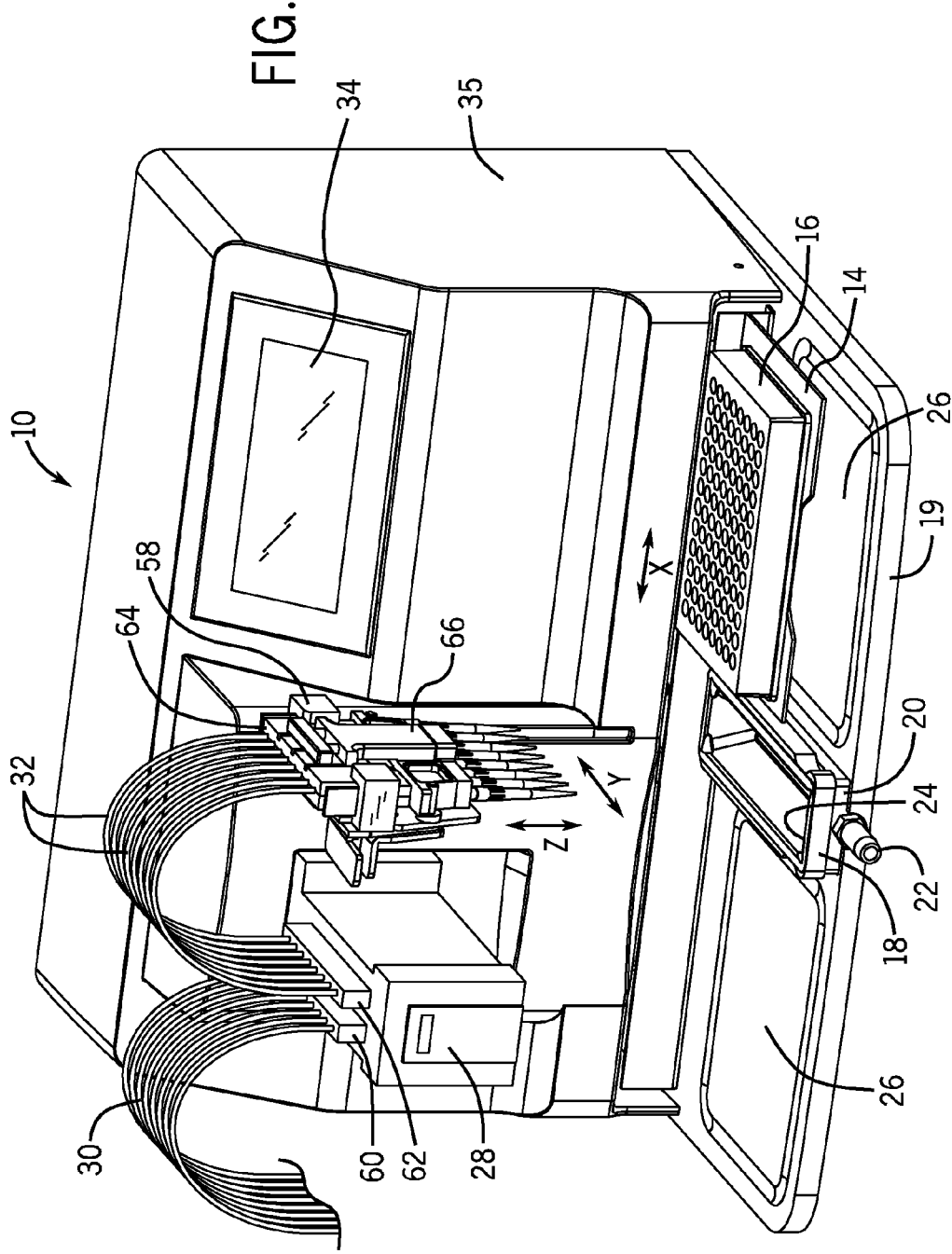
FIG. 1 is a perspective view of a multi-channel wellplate filling station constructed in accordance with an exemplary embodiment of the invention. The multi-channel wellplate filling station is shown in FIG. 1 to be set up in pipette tip mode.

Referring to FIG. 1, the multi-channel wellplate filling station 10 includes a wellplate platform 14 that is repositionable along a horizontal X-axis. In FIG. 1, a wellplate 16 having ninety six (96) channels is placed on the repositionable wellplate platform 14. The wellplate 16, as known in the art, has standardized dimensions in accordance with the SBS format, and has eight (8) rows and twelve (12) columns of wells. The platform 14 includes an indentation or other means for precisely positioning the wellplate 16 in a predetermined location relative to the repositionable platform 14. The system 10 also includes a reagent reservoir 18 that is mounted to or integral with a station base plate 19. The base of the reagent reservoir 18 preferably consists of a waste trough 20 having a waste port 22 that would normally be connected to tubing in order to redirect liquid waste from the waste trough to a waste container. In accordance with the preferred embodiment of the invention, a watertight liner 24 is placed in the waste trough 20. A suitable liner is shown and described in U.S. Pat. No. 7,811,522, which is entitled "Sample Reservoir Kits with Disposable Liners" issuing to Mathus et al on Oct. 12, 2010, which is herein incorporated by reference. Other reagent reservoirs or reservoir systems may be used without departing from the spirit of the invention. The base plate 19 preferably includes sunken spill basins 26 on either side of the liquid reservoir to facilitate clean up in the event of spillage.

Figure 6:
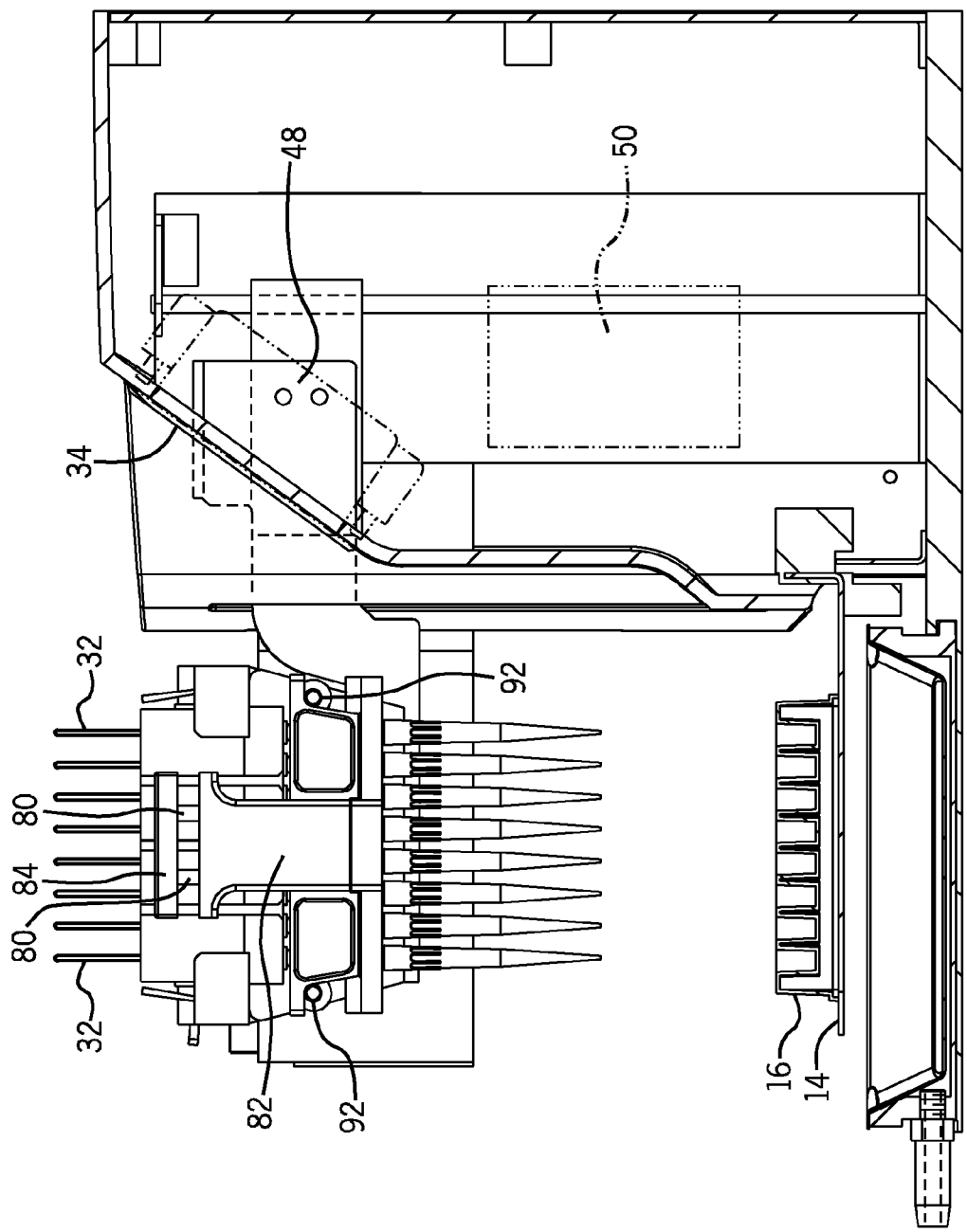
FIG. 6 is a sectional view taken along line 6-6 in FIG. 3.

The system 10 includes a touch screen user interface 34 for programming the operation of the unit. An electronic control unit 48 is shown in phantom in FIG. 6. FIG. 6 also shows in phantom a power supply 50. The programming of the system 10 through the user interface 34 necessarily corresponds to the mode for which the system 10, 10F, 10W is set up namely, pipetting mode, flow-through mode, or wash station mode.

The primary purpose of the multi-channel wellplate filling system 10 as set up in FIG. 1 is to aspirate liquid reagent contained in the reagent reservoir 18 into the array of multiple pipette tips 12, and then dispense the aspirated liquid reagent into wells in the wellplate 16 one column at a time. The pipette tips are arranged in a linear array extending along a Y-axis that is perpendicular to the X-axis along which the wellplate 16 is repositioned. More particularly, the system 10 includes multiple pipette tip mounting shafts (not shown in FIG. 1) that are arranged in a linear array extending along the Y-axis onto which pipette tips are loaded. In the eight (8) channel system illustrated in FIG. 1, the center line to center line spacing between each tip mounting shaft, and hence between each pipette tip 12, is nine (9) millimeters corresponding to the center line to center line spacing in the wells of a standard 96 wellplate. The head for the tip mounting shafts and the pipette tips 12 is movable vertically along a Z-axis. Also, in the exemplary embodiment the pipetting head is movable as a unit in the Y-axis direction for a relatively short distance, primarily in order to accommodate filling of 384 wellplates or even 1536 wellplates. In order to fill the wells in the wellplate 16, the pipette tips 12 are lowered vertically into the liquid reagent contained in the reservoir 18. The system 10 is then operated to aspirate liquid into the pipette tips 12. The pipette tips 12 are then vertically raised and the wellplate platform 14 and the wellplate 16 are repositioned in the X-axis direction to position a selected column of wells underneath the array of pipette tips 12. The pipette tips 12 are then lowered vertically so that the distal ends of the pipette tips are within or slightly above the aligned respective well on the wellplate 16. At this point, the system then dispenses a selected amount of liquid reagent into the respective column of wells. Preferably, as will be discussed in more detail later, the system implements a touch-off protocol that automatically touches off each pipette tip 12 on the wall of the respective well in order to ensure full accurate dispensing of the desired amount. The pipette tips 12 are then raised to clear the wellplate 16, and the wellplate 16 is indexed along the X-axis to align the next selected column of wells with the array of pipette tips and the process is repeated. In order to dispense into the wellplate 16, the platform 14 and wellplate 16 will be moved to reside over the reagent reservoir 18. If it is necessary to aspirate additional liquid from the reagent reservoir 18 into the pipette tips before all of the wells in the wellplate 16 have been filled, the system moves the wellplate platform 14 and the wellplate 16 to the right to clear the path to the reagent reservoir 18 for the pipette tips 12. Once additional liquid is aspirated into the pipette tips 12, the wellplate platform 14 and wellplate 16 are repositioned under the pipette tips 12 in order to continue dispensing into the appropriate wells on the wellplate 16.

The system 10 can also be used to aspirate liquid from a column of wells on wellplate 16 into the array of pipette tips 12. In this case, the aspirated liquid can then be dispensed into the waste trough 20, i.e., reagent reservoir 18 without the liner 24, or if desired into the liner 24. The ability to aspirate liquid reagent into the pipette tips 12 further enables the system 10 to be programmed to conduct serial dilutions. For example, the system 10 is programmed to initially to fill all of the wells in the wellplate 16 with a determined amount of a first solution, e.g. 90 microliters of solution A. Then, the reagent in the reservoir 18 is replaced with another solution, e.g. solution B, and the system is programmed to pipette a predetermined amount of solution B (e.g., 10 microliters of solution B) in the first column of wells on the wellplate, thereby producing a mixture with a 10% concentration of solution B. The system 10 then aspirates 10 microliters of the 10% solution from the first column of wells and dispenses in the second column of wells to result in a mixture having a 1% concentration of solution B. This automated procedure of aspirating and dispensing into the next column of wells on the wellplate is executed for all the columns on the wellplate if desired. While serial dilutions are typically done in the art using handheld pipettors or on automated liquid handling equipment, conventional flow-through wellplate filling stations are not capable of conducting serial dilutions as described.

As shown in FIG. 1 as well as the other figures, the system 10 includes a peristaltic pump 28 through which a tubing set 30 having multiple flexible tubes 32 is mounted. The peristaltic pump 28 pumps fluid through the flexible tubes 30, either air or liquid reagent, depending on the mode of use. When the system 10F, FIG. 11 is set up to operate in flow-through mode as in the prior art, the peristaltic pump 28 pumps liquid reagent through the flexible tubing to a filling nozzle head as will be discussed in more detail later with respect to FIG. 11. However, when the system is set up to operate with pipette tips 12, the peristaltic pump 28 will normally pump only air through the flexible tubes 32 of the tubing set 30. In order to aspirate liquid from the reagent reservoir 18 into the pipette tips 12, the peristaltic pump 28 is operated in reverse to create suction. The peristaltic pump 28 is then operated in the forward direction to dispense selected amounts of liquid from the pipette tips 12. The operation of the peristaltic pump is calibrated in order to compensate for aspiration and dispensing volumes, and volume anomalies which may otherwise tend to occur. The tubing set 30 is preferably calibrated at the factory by setting the pre-stretch header 60, 62. It is particularly desirable to use an encoder to monitor the position of the peristaltic pump especially to account for volume variability due to partial rotation of the peristaltic pump. Although the system 10, when set up as shown in FIG. 1, will normally be programmed to aspirate and dispense from the pipette tips 12; it is possible to run the system in flow-through mode where liquid reagent is pumped from a reagent bottle through the flexible tubes 32 and through the pipette tips 12.

Figure 2:
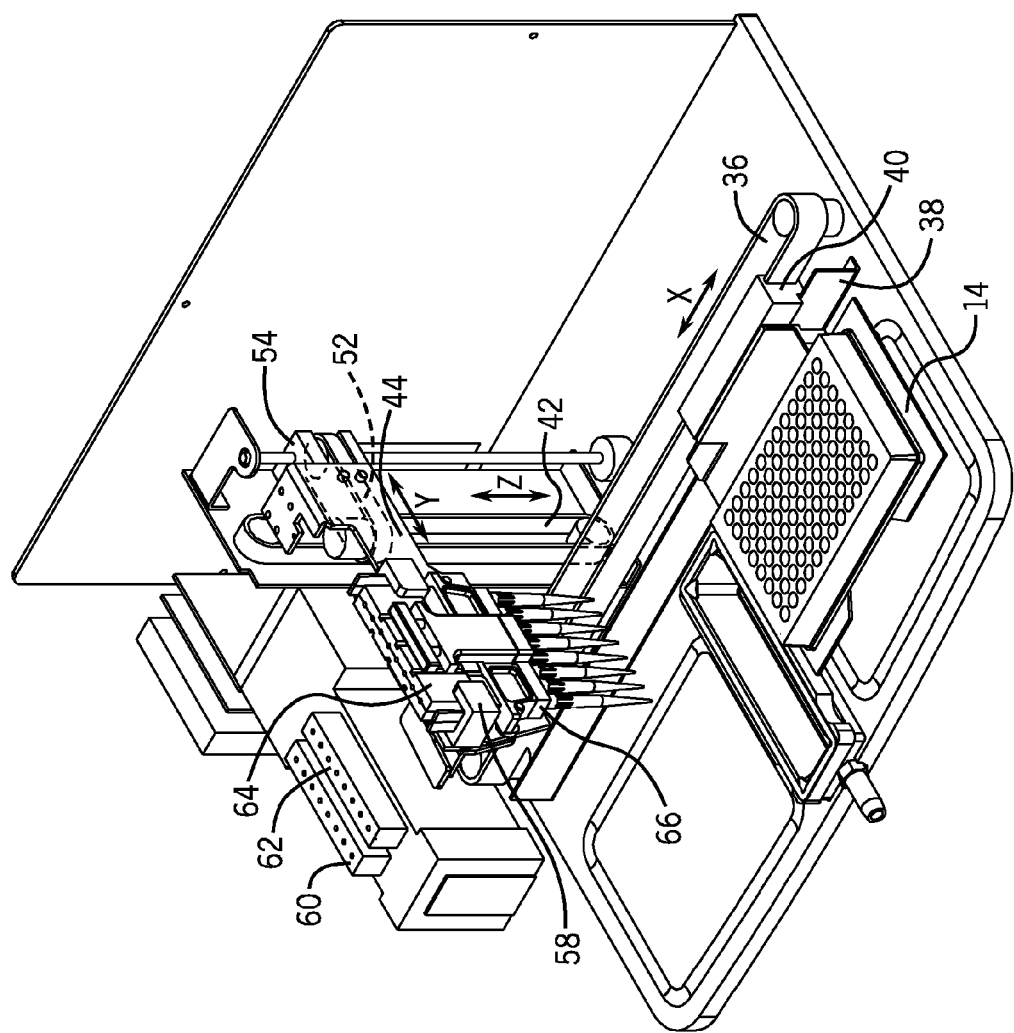
FIG. 2 is a view of the multi-channel wellplate filling station shown in FIG. 1 with the housing removed in order to show internal components of the system.

FIG. 2 shows the system 10 with the housing 35 removed and other components removed in order to better illustrate the drive mechanisms. Referring to FIG. 2, the system 10 includes an X-axis belt drive 36. A stepper motor (not shown) located on the left hand side of the unit 10 drives the X-axis belt drive 36 in response to instruction from the electronic control unit 48 (FIG. 6). The belt 36 is clamped to a linear bearing 40 that rides on a linear rail 38 for the X-axis drive. The wellplate platform 14 is attached to the bearing 40 and is repositioned along the X-axis rail 38 as the stepper motor moves the X-axis belt drive 36 under the direction of the electronic control unit 48 as programmed through the user interface 34 (see FIGS. 1 and 6). A Z-axis belt drive 42 is clamped to a cartridge support body 54. A stepper motor (not shown) operates the Z-axis belt drive 42 under the direction of the programmed control unit in order to vertically lift and lower the pipetting head. The cartridge support body 54 moves vertically along the Z-axis but does not move horizontally in either the X-axis or Y-axis direction. A cartridge support arm 44 is mounted for Y-axis movement via a rail connected to cartridge support body 54. A Y-axis belt drive 52 moves the cartridge support arm 44 in the Y-axis direction, preferably no more than about twenty (20) millimeters. A Y-axis stepper motor (not shown) drives the Y-axis belt drive 52 under the direction of the control unit 48.

Now referring to both FIGS. 1 and 2, a cartridge holder 58 is mounted to the cartridge support arm 44. The tube set 30 as mentioned includes multiple flexible tubes 32 as well as headers 60, 62 for mounting the tube set 30 to the peristaltic pump 28. The tube set also includes, in this exemplary embodiment, a interfacing nozzle cartridge 64 at the distal end of the flexible tubes 32. The interfacing nozzle cartridge 64 is held in the cartridge holder 58 that is mounted to the support arm 40. A separate removable cartridge 66, which is referred to herein as the tip mounting shaft cartridge, is separately removable from the system 10. The tip mounting shaft cartridge 66 is attachable to the interfacing nozzle cartridge 64 such that each pipette tip mounting shaft 68 on the mounting shaft cartridge 66 is in fluid communication with a respective interfacing nozzle and flexible tube pair.

Figure 10:
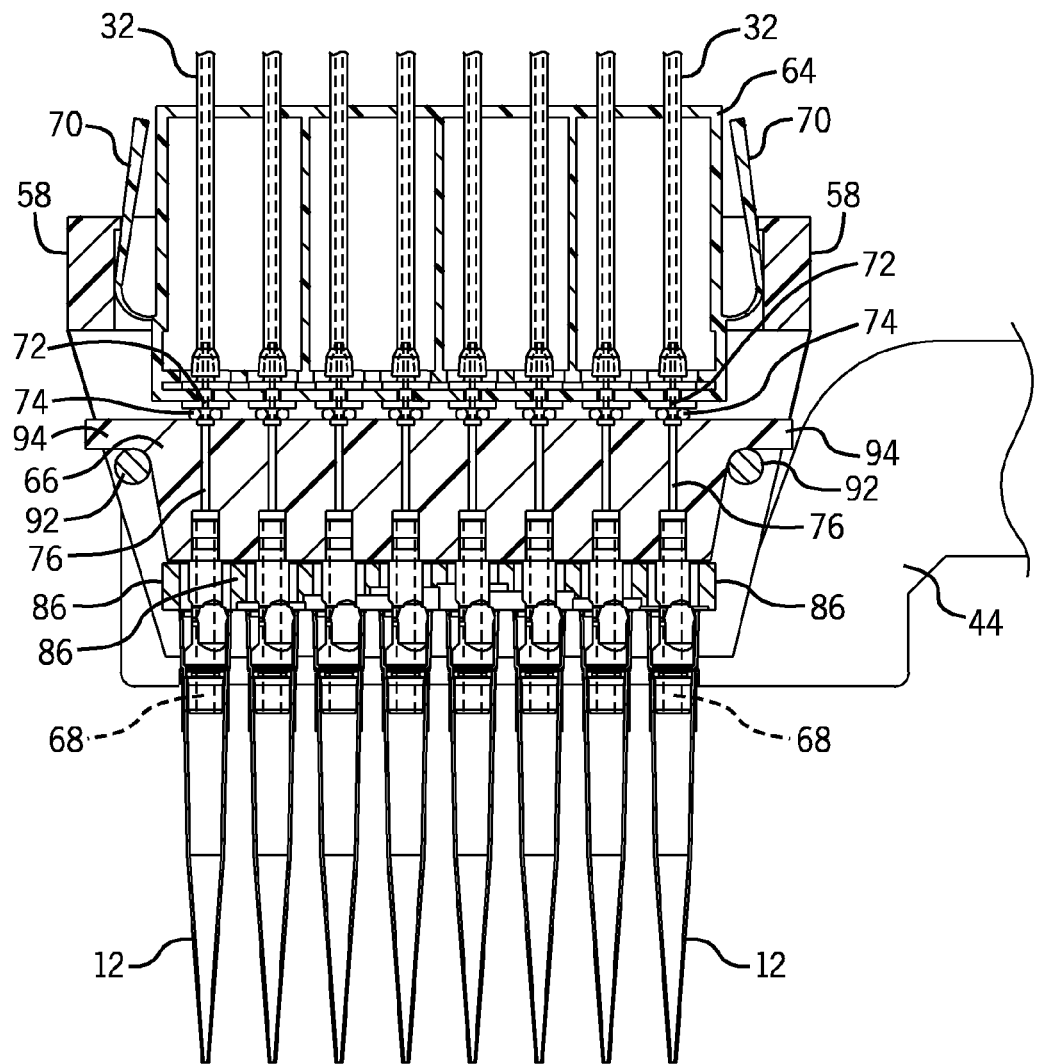
FIG. 10 is a detailed view of the pipette tip mounting shaft cartridge attached to a interfacing nozzle cartridge in accordance with an exemplary embodiment of the invention.

The configuration and mounting of the interfacing nozzle cartridge 64 and the tip mounting shaft cartridge 66 are now described in more detail with respect to FIGS. 6 and 10. Referring first to the interfacing nozzle cartridge 64, finger pinch members 70 are provided to secure the interfacing nozzle cartridge 64 in the cartridge holder 58 mounted to the support arm 44. The cross-sectional view in FIG. 10 shows the flexible tubes 32 being mounted to the cartridge 64 and placed in fluid communication with the interfacing nozzles 72. The interfacing nozzles 72 are similar to conventional filling nozzles for flow-through multi-channel wellplate filling systems of this type, however, the nozzles are relatively short, e.g., ¹⁄₁₆ of an inch. Filling nozzles in conventional systems are normally at least about ¼ of an inch in length in order to prevent the dispensed fluid from spraying. As shown best in FIG. 10, elastomeric seals, such as sealing rings 74 or a gasket, are provided at the outlet of the interfacing nozzles 72.

The tip mounting shaft cartridge 66 is a physically separate component that is preferably designed to be easily removable from the system in order to facilitate convenient loading and ejection of the pipette tips 12. The body of the tip mounting shaft cartridge 66 includes a plurality of fluid conduits 76 which lead to respective pipette tip fittings 68 that are permanently attached to the cartridge 66. While any suitable pipette tip fittings are contemplated within the scope of the invention, the preferred pipette tip fittings 68 are configured in accordance with that described in U.S. Pat. No. 7,662,343 entitled "Locking Pipette Tip and Mounting Shaft", by Mathus et al issuing on Feb. 16, 2010 or U.S. Pat. No. 7,662,344 entitled "Locking Pipette Tip and Mounting Shaft", by Mathus et al issuing on Feb. 16, 2010, U.S. patent application Ser. No. 12/568,801 entitled "Pipette Tip Mounting Shaft" by Terrence Kelly et al, filed on Sep. 29, 2009, all of which are assigned to the signing of the present application and are herein incorporated by reference. The tip mounting shaft cartridge 66 also includes a stripping mechanism 78, see FIG. 6. The stripping mechanism 78 includes two (2) spring-biased, stepped shafts 80 passing through rod guide 82 on the tip mounting shaft cartridge 66. A stripping button 84 is mounted to the top end of the spring-biased rods 80. A pipette tip stripping plate 86 is attached to the lower end of the spring-biased rods 80. The stripping plate 86 is shown in cross-section in FIG. 10, and has openings through which the upper end of the pipette tip mounting shafts 68 pass. In FIG. 10, the stripping plate 86 is shown in the normally biased upward position at a location above the normal location of the top end of the pipette tips 12 loaded onto the mounting shafts 68. FIG. 6 shows the button 84 in the normally biased upward position. In order to eject pipette tips from the cartridge 66, the user removes the cartridge 66 from the system 10 and pushes the button 84 downward against the spring bias to lower the stripping plate 86 and eject the tips 12 from the mounting shafts 68.

The removability of the pipette tip mounting shaft cartridge 66 also facilitates convenient loading of pipette tips 12. Once tips 12 are loaded, the cartridge is then mounted and clamped into the system 10 for use. The pipette tip mounting shaft cartridge 66 preferably includes a magnet in order to help hold the cartridge 66 against the support arm 44. A clamping mechanism secures the pipette tip mounting shaft cartridge 66 in sealed fluid communication with the interfacing nozzle cartridge 64. FIG. 10, in particular, illustrates that each mounting shaft 68 and pipette tip 12 is in sealed fluid communication with a respective interfacing nozzle 72 and flexible tube 32 when the tip mounting shaft cartridge 66 is attached to the system and clamped or latched to the interfacing nozzle cartridge 64.

Figure 3:
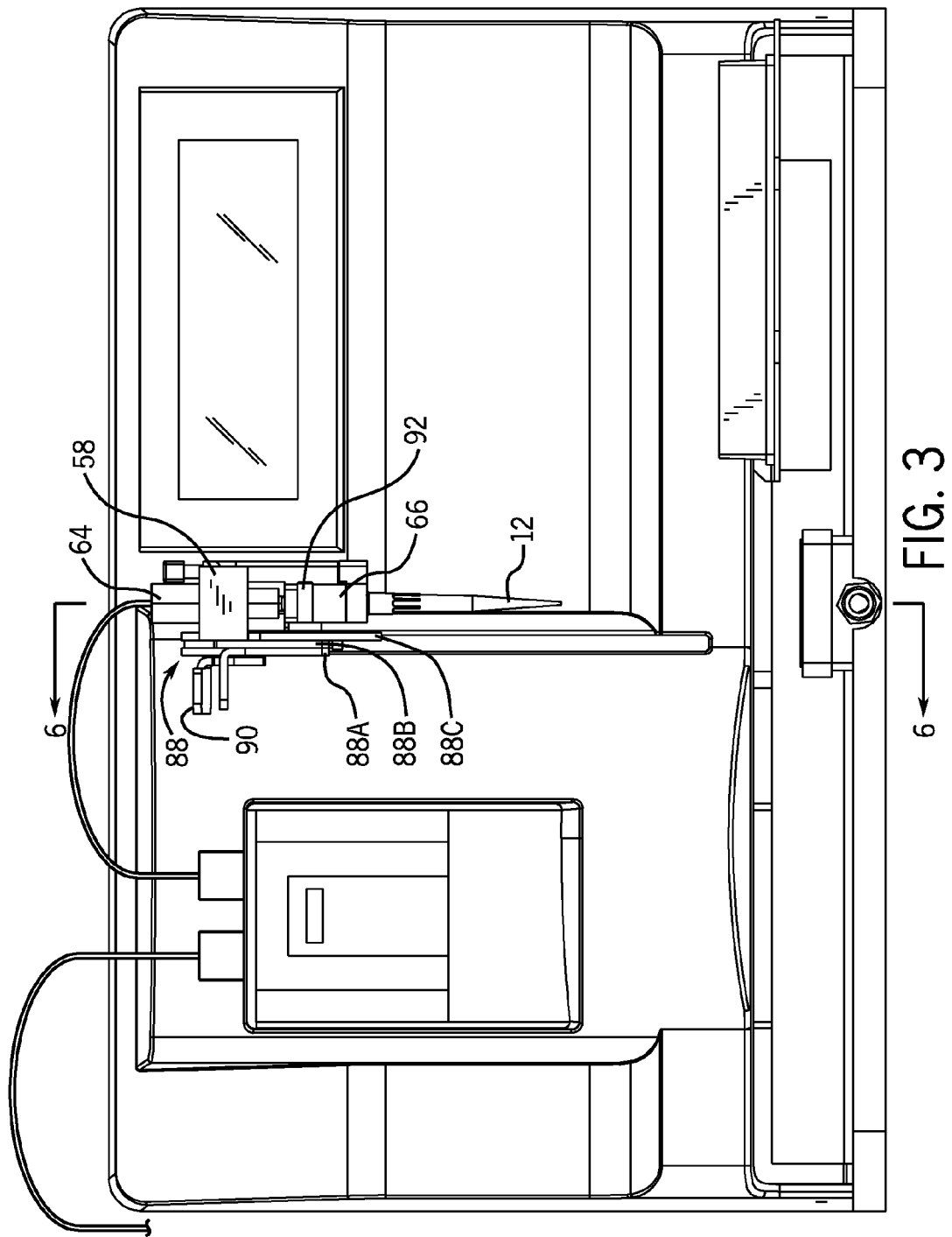
FIG. 3 is a front elevation view of the multi-channel wellplate filling system shown in FIG. 1.

Referring now also to FIG. 3, the clamping mechanism 88 in the exemplary embodiment includes three (3) plates, see Ref. Nos. 88a, 88b and 88c in FIG. 3. A clamp lever 90 rotates a clamp bearing (not specifically shown) that passes through the three (3) plates 88a, 88b and 88c. The clamp bearing rotates concentrically within the outer plates 88a, 88c, but includes an eccentric cam corresponding to the location of the middle plate 88b. The cartridge holder 58 is mounted to the middle plate 88b, see FIG. 3. Posts 92 extend outward from outer plate 88c and are fixed in relation to the support arm 44. As shown in FIGS. 6 and 10, the tip mounting shaft cartridge 66 includes flanges 94 that are designed to sit on the posts 92 and hold the cartridge 66 in fixed relation to the plate 88c in conjunction with the magnet. Note that the posts 92 not only hold the cartridge 66 in the appropriate vertical position, but also align the cartridge 66 in the appropriate horizontal direction. With the tip mounting shaft cartridge 66 in position as shown in FIG. 10, the clamp lever 90 is then rotated into the position shown in FIG. 3 in order operate the eccentric cam and move the interfacing nozzle cartridge 64 downward and compress the seals 74 or gasket against the top surface of the tip mounting shaft cartridge 66. One of ordinary skill in the art will appreciate that other clamping mechanisms may be suitable for implementing the invention.

Figure 4:
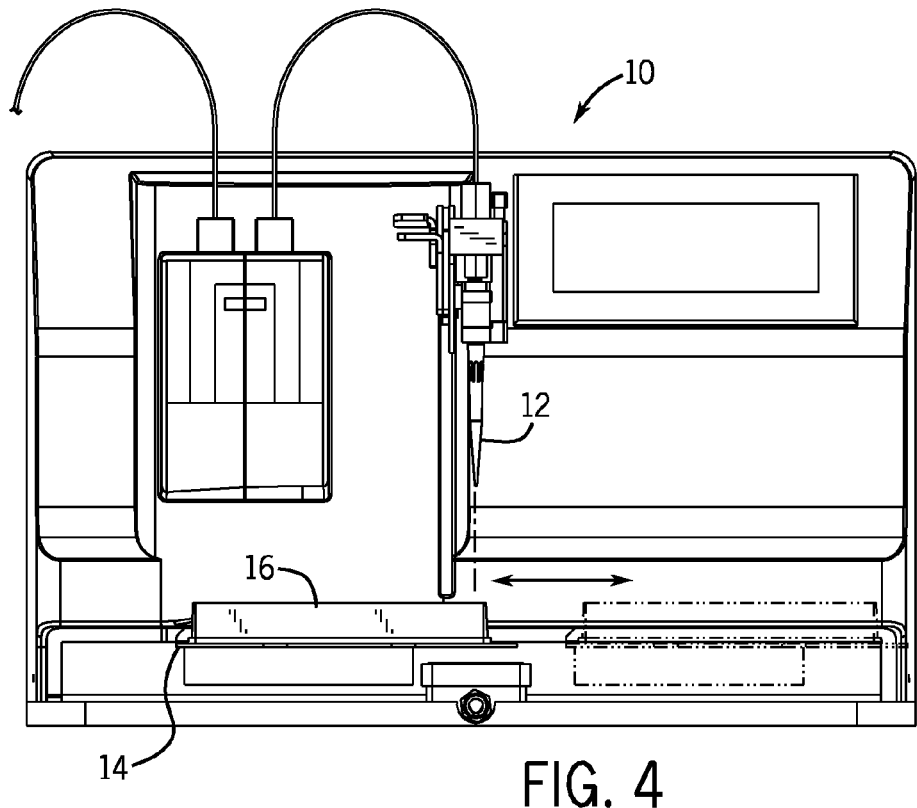
FIG. 4 is a schematic view illustrating X-axis movement of a wellplate placed in the station.
Figure 5:
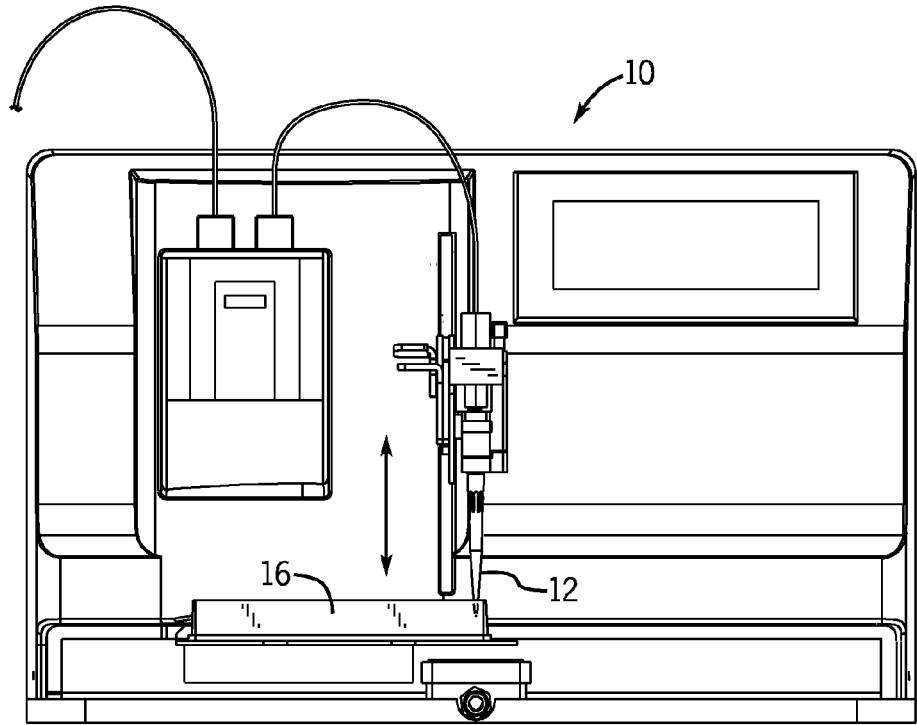
FIG. 5 is a schematic view illustrating Z-axis movement of the pipetting head.
Figure 7:
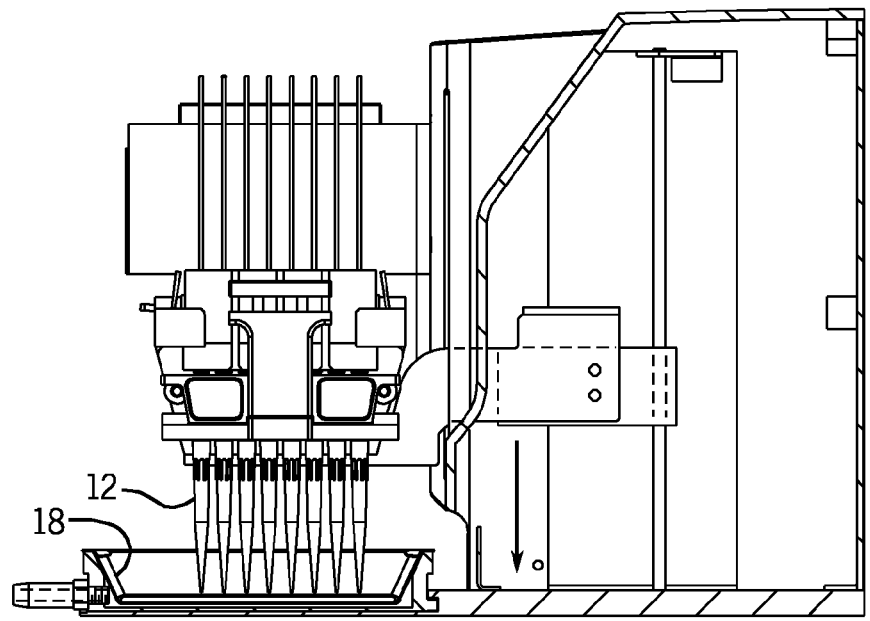
FIG. 7 is a schematic view illustrating the lowering of the pipetting head so pipette tips are positioned to aspirate liquid reagent from a reagent reservoir located on the station.
Figure 8:
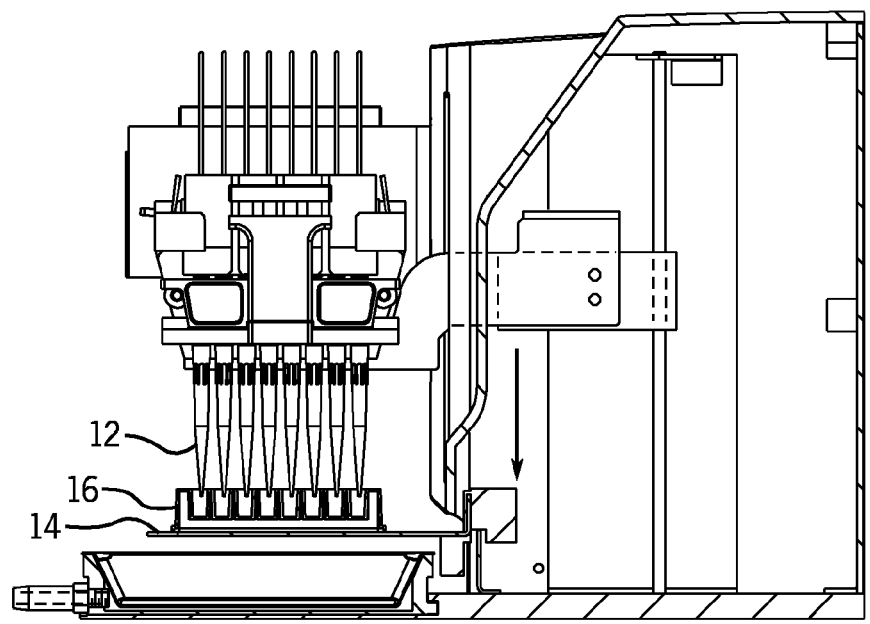
FIG. 8 is a schematic view illustrating pipette tips positioned to dispense liquid reagent into wells on a wellplate loaded on the station.
Figure 9:
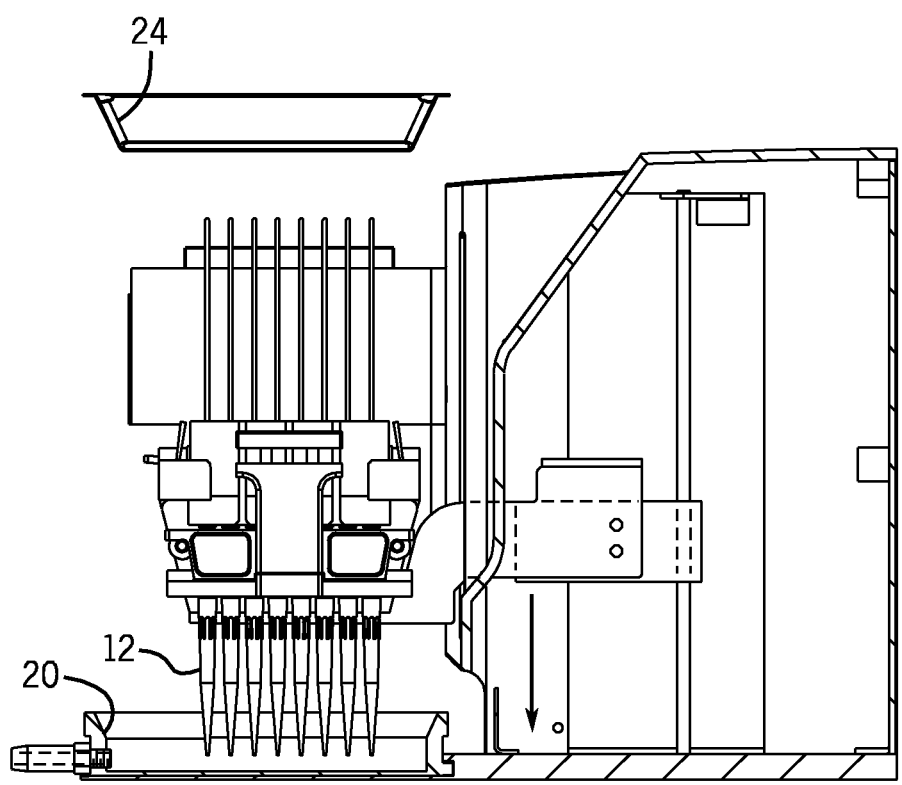
FIG. 9 is a schematic view illustrating pipette tips lowered in order to dispense liquid into a waste trough on the station.

The exemplary steps of operation of the system 10 when set up in pipetting mode are illustrated in FIGS. 4-9. FIG. 4 schematically illustrates the system 10 moving the wellplate platform 14 and a wellplate 16 in the X-axis direction in order to align a column of wells in the wellplate 16 underneath the array of pipette tips 12. FIG. 5 illustrates movement of the array of pipette tips 12 in the vertical Z-axis direction in order to place the tips 12 in an appropriate position for dispensing liquid into a column of wells in the wellplate 16. FIG. 7 illustrates the pipette tips 12 being lowered into a reagent reservoir 18, for example, in order to aspirate liquid from the reservoir 18 into the pipette tips 12. FIG. 8 shows the pipette tips 12 being lowered into position over a wellplate 16 in order to dispense fluid from the tips 12 into the wells in the wellplate 16. The pipette tips 12 must be raised from the position shown in FIG. 7 to clear the reservoir and the space needed for the wellplate platform 14 and wellplate 16 to be moved along the X-axis horizontally under the plane of the pipette tips 12 before lowering the pipette tips 12 into the position shown in FIG. 8. FIG. 9 illustrates the pipette tips 12 lowered into a position similar to that shown in FIG. 7, however, in FIG. 9 the removable liner 24 has been removed from the waste trough 20 thereby converting the location from a reagent reservoir 18 into a waste trough 20.

While the system shown in the drawings is an 8-channel system with a center line to center line spacing between the pipette tips of 9 millimeters, the system may be constructed with more or less channels with the same or different center line to center line spacing. For example, a 16-channel system having a center line to center line spacing of 4.5 millimeters would be suitable for 384 wellplates, or even 1536 wellplates if the system includes a Y-axis drive to reposition the pipette tips in the Y-axis direction. In the 8-channel system, a disposable pipette tips capable of aspirating and dispensing up to 300 microliters would be suitable for many applications. In the 16-channel system, disposable pipette tips 12 capable of aspirating and dispensing up to 125 microliters would be suitable for many applications. Larger volume pipette tips may be desirable for use with deep wellplates. The diameter of the tubing sets should likewise be adjusted to improve accuracy depending on the volume of the pipette tips. For example, flexible tubing 32 with an inside diameter of 1.2 mm is suitable for 300 mL pipette tips and flexible tubing 32 with an inside diameter of 0.5 mm is suitable for 125 mL pipette tips.

As mentioned, the electronic control unit 48 desirably contains software to coordinate movement of the X-axis, Z-axis and/or Y-axis drive systems in order to direct the system to touch-off drops of liquid at the end of the respective pipette tips into a column of wells on the wellplate after dispensing liquid into the column of wells. If desirable, the option to touch-off can be provided as a feature selected by the user via the user interface 34, although in most cases, it is believed that touching-off will be the norm when pipette tips 12 and should be an automatic feature.

Referring now to FIGS. 11 and 12, the system 10F is set up for flow-through filling of the wellplate 16. In particular, the tube set 130 is quite similar to the tube set 30 used in FIG. 1, except as mentioned before the interfacing nozzles are preferably at least ¼ of an inch long, see FIG. 12. In FIG. 11, the ends of the flexible tubes 132 are placed in a reagent bottle 100, and the system is operated in many ways similar to prior art wellplate filling stations. The peristaltic pump 28 is run in order to prime the tube set 130 and the filling nozzles 172, and then preferably the first dispense is dispensed into the waste trough 20 (without a liner 24) in order to ensure accuracy of the following dispenses. Then, the system is operated to dispense through the filling nozzles 172 into respective columns of the wellplate 16 as the wellplate 16 and platform 14 are indexed along the X-axis below the array of filling nozzles 172. FIG. 11 also shows a second peristaltic pump 102 which is preferably controlled by the system control unit 48 for the purpose of mixing liquid reagent within the reagent bottle 100. The second peristaltic pump 102 pumps liquid through mixing tube 104. Both ends of the mixing tube 104 are located in the reagent bottle 100, and the control unit 48 periodically or continuously runs the peristaltic pump 102 in order to mix the contents within the reagent bottle as desired.

Referring now to FIG. 13, the system 10W is schematically illustrated to be set up as a wellplate wash station. To do this, the tube set is replaced with a wash station cartridge and tube set 230, 264. The wash station cartridge 264 is mounted on the support arm 44 and cartridge holder 58 and includes pairs of needles consisting of a wash needle 265 and a vacuum needle 266 for each channel, e.g. eight (8) pairs of wash and vacuum needles for an 8-channel system. In each pair of needles, the vacuum needle 266 extends downward beyond the wash needle 265. As shown in FIG. 13, each of the vacuum needles 266 is in fluid communication with a vacuum manifold 268, which desirably constitutes part of the wash station cartridge. The vacuum manifold 268 includes a port 270 that is connected to a first vacuum tube 272. The first vacuum tube 272 passes through a solenoid activated pinch valve 274 and is attached to a sealed vacuum waste container 276. A second vacuum tube 278 is attached to the sealed vacuum waste container 276 and is connected to vacuum pump 280. A self-sealing filter 282 is preferably located in the second vacuum line 278 upstream of the vacuum pump 280 in order to protect the pump from liquid waste contamination. The system 10W also includes a wash solution hose 284 that leads to a manifold 286 that redistributes the wash fluid among the flexible tubes 232 of the tubing set 230. In this regard, the peristaltic pump 28 pumps wash fluid from the bottle 288 of washing fluid to the wash needles 265 in much the same manner that the system 10F pumps liquid reagent to the filling nozzles when set up in the flow-through mode. As shown in FIG. 13, the system 10W also preferably includes a bottle 290 of rinsing fluid. An electronically controlled valve 292 connects the input to the manifold 286 to either the container 288 containing the wash fluid or the container 290 containing the rinsing fluid. The electronic components including the vacuum pump 280, the valves 292 and 274 and a power supply are contained in a separate box having an RS232 or USB port to communicate electronically with the control unit 48 in the main housing. Desirably, the box also includes necessary ports for the vacuum pump 280, and the wash 288 and the rinse 290 containers as well as an output port to the tube set 230.

To operate the wash station, the controller 48 directs the system to lower the needle pairs 265, 266 into the respective wells. The peristaltic pump 28 is activated to pump washing fluid from the container 288 into the respective array of wells on the wellplate through the wash needles 265, and then vacuum pump 280 is activated and the pinch valve 274 is opened. To vacuum, the controller directs the X-axis and Y-axis drive mechanisms to move the needle pairs horizontally around the respective wells in a relative circular motion. In other words, the needle pairs 265, 266 are directed to move in the X-axis direction while at the same time the wellplate 16 on the wellplate platform 14 is directed to move in the Y-axis direction, both oscillating in a coordinated manner in order for the needle pairs 265, 266 to move in a relative circular motion with respect to the respective well. The washing fluid in each well is picked up by the vacuum needles 266 and dropped into the vacuum waste container 276. The pinch valve 274 is activated and deactivated in order to assure that sufficient vacuum has built up in the vacuum waste container 276 to enable reliable suction at the vacuum needles 266. After one column of wells in the wellplate has been washed, the system 10W moves to the next column, or in the case of a 384 wellplate can move to a set of additional wells in the same column on the wellplate 16. Once the washing function has been complete, the system automatically switches valve 292 to a rinsing fluid, such as water or saline to rinse the tube set and the needles.

Those skilled in the art will appreciate that the system 10, 10F and 10W contains several features, many of which can be practiced independently of one another.

The invention claimed is:

1. A multi-channel wellplate filling system comprising:
    a repositionable wellplate platform for holding a multiwell plate;
    a motorized x-axis drive mechanism for repositioning a wellplate platform horizontally along an x-axis;
    a tubing set having multiple flexible tubes, having a first end and a second end, wherein the first end is open to the environment;
    a peristaltic pump that pumps liquid or air through the flexible tubes in a forward direction and in a reverse direction;
    multiple pipette tip mounting shafts arranged in a linear array extending along a y-axis that is perpendicular to the x-axis, each pipette tip mounting shaft being in fluid communication with a second end of the respective flexible tube of the tubing set and being adapted to receive a disposable pipette tip; and
    a controller having a user interface and programmed to operate the multi-channel wellplate filling system in a pipetting mode to aspirate liquid into the disposable pipette tips mounted on the pipette tip mounting shafts and dispense liquid from the disposable pipette tips into wells in a multiwall plate on the repositionable wellplate platform,
    wherein when in the pipetting mode, the first ends of the multiple flexible tubes in the tube set are open to the environment, and when the controller is programmed in the pipetting mode the controller operates the peristaltic pump to pump air only from the first open ends through the flexible tubes in a reverse direction to create suction and aspirate liquid into the disposable pipette tips, and pumps in a forward direction to dispense selected amounts of liquid from the disposable pipette tips.

2. A multi-channel wellplate filling system as recited in claim 1 wherein the multiple pipette tip mounting shafts are located at a fixed x-axis location.

3. A multi-channel wellplate filling system as recited in claim 1 further comprising a reagent reservoir located below the array of pipette tip mounting shafts.

4. A multi-channel wellplate filling system as recited in claim 1 wherein the tubing set includes a nozzle cartridge having a plurality of interfacing nozzles and the flexible tubes in the tube set are connected to the cartridge so that the fluid flows from the flexible tubes to respective interfacing nozzles; and further wherein the linear array of pipette tip mounting shafts are on a mounting shaft cartridge that is attachable to the nozzle cartridge such that each mounting shaft is in fluid communication with a respective interfacing nozzle and flexible tube pair.

5. A multi-channel wellplate filling system as recited in claim 4 further comprising a latching mechanism for attaching the pipette tip mounting shaft cartridge to the interfacing nozzle cartridge.

6. A multi-channel wellplate filling system as recited in claim 5 further comprising elastomeric sealing material between the interfacing nozzle cartridge and the mounting shaft cartridge.

7. A multi-channel wellplate filling system as recited in claim 4 wherein the pipette tip mounting shaft cartridge includes a mechanism to strip disposable pipette tips from the mounting shafts on the cartridge.

8. A multi-channel wellplate filling system as recited in claim 1 further comprising a motorized, z-axis drive mechanism that moves the linear array of pipette tip mounting shafts in a vertical up or down direction.

9. A multi-channel wellplate filling system as recited in claim 8 further comprising a motorized y-axis drive mechanism that moves the linear array of pipette tip mounting shafts horizontally along the y-axis in order to reposition the pipette tip mounting shafts to different wells located at the same x-axis location when a multiwell plate is located in a selected x-axis position.

10. A multi-channel wellplate filling system as recited in claim 3 further comprising at least one disposable liner for the reagent reservoir.

11. A multi-channel wellplate filling system as recited in claim 1 wherein the controller contains software to direct the system to touch off drops of liquid from one end of respective pipette tips into an array of wells on a wellplate after dispensing liquid into the array of wells.

12. A multi-channel wellplate filling system as recited in claim 1 wherein the controller contains software to direct the system to conduct serial dilutions in respective wells on a wellplate placed in the system.

13. A multi-channel wellplate filling system as recited in claim 1 wherein the pipette tip mounting shafts are spaced apart at a centerline to centerline distance of 9 millimeters.

14. A multi-channel wellplate filling system as recited in claim 1 wherein the pipette tip mounting shafts are spaced apart at a centerline to centerline distance of 4.5 millimeters.

15. A multi-channel wellplate filling system as recited in claim 1 wherein the position of the wellplate platform in the x-direction is indexed by the x-axis drive mechanism so that the linear array of pipette tip mounting shafts are aligned with a selected column of wells in a wellplate on the platform.

16. A multi-channel wellplate filling system as recited in claim 1 wherein the flexible tubes are calibrated by adjusting tubing pre-stretch.

17. A multi-channel wellplate filling system as recited in claim 1 wherein the system is an 8-channel system including 8 pipette tip mounting shafts arranged in a linear array along the y-axis, and disposable pipette tips are capable of aspirating and dispensing up to 300 microliters.

18. A multi-channel wellplate filling system as recited in claim 1 wherein the system is a 16-channel system including 16 pipette tip mounting shafts arranged in a linear array along the y-axis, and the disposable pipette tips are capable of aspirating and dispensing up to 125 microliters.

19. A multi-channel wellplate filling system as recited in claim 2 wherein the system is an 8-channel system including 8 pipette tip mounting shafts arranged in a linear array along the y-axis, and the controller is further programmed to operate the system in a lfow through mode to dispense liquid from the flexible tubes and disposable pipette tips into wells in the multiwall plate on the repositionable wellplate platform, wherein the peristaltic liquid only through the flexible tubes when operating in the flow-through mode and in the forward direction to dispense a selected amount of liquid from the disposable pipette tips when in the flow-through mode.

20. A multi-channel wellplate filling system as recited in claim 1 wherein the system is a 16-channel system including 16 pipette tip mounting shafts arranged in a linear aray along the y-axis, and the controller is further programmed to operate the system in a lfow through mode to dispense liquid from the flexible tubes and disposable pipette tips into wells in the multiwall plate on the repositionable wellplate platform, wherein the peristaltic liquid only through the flexible tubes when operating in the flow-through mode and pumps in the forward direction to dispense a selected amount of liquid from the disposable pipette tips when in the flow-through mode.

21. A multi-channel wellplate filling system as recited in claim 1 further comprising:
 a plate washing head having multiple pairs of needles comprising a wash needle and a vacuum needle, the multiple pairs of needles being arranged in a linear array;
 a second tube set having multiple flexible tubes in fluid communication with the wash needles on the plate washing head;
 a vacuum source in fluid communication with the vacuum needles on the plate washing head;
 wherein the controller is further programmed to operate in wash mode in which the peristaltic pump pumps wash fluid through the flexible tubes in the tubing set through the wash needles on the plate washing head.

22. A multi-channel wellplate filling system as recited in claim 21 wherein the vacuum needle in each pair of needles extends further down that the wash needle.

23. A multi-channel wellplate filling system as recited in claim 21 further comprising a z-axis drive mechanism that moves the plate washing head in a vertical up and down direction.

24. A multi-channel wellplate filling system as recited in claim 23 wherein the x-axis position of the wellplate platform is indexed by the x-axis drive mechanism so that the linear array of needles pairs are aligned with a selected column of wells in a wellplate on the repositionable wellplate platform.

25. A multi-channel wellplate filling system as recited in claim 24 further comprising a y-axis drive mechanism that moves the plate washing head in a horizontal direction perpendicular to the horizontal x-axis direction.

26. A multi-channel wellplate filling system as recited in claim 25 further comprising a controller that is programmed to move the linear array of needle pairs downward into aligned wells in a column of a multiwell plate on the repositionable wellplate platform and then move each needle pair and the repositionable wellplate platform to move the needle pairs relative to the respective well horizontally around the respective well in a relative circular motion.

27. A multi-channel wellplate filling system as recited in claim 1 further comprising:
 a second peristaltic pump with at least one mixing tube, wherein both ends of the mixing tube are located in a liquid mixture contained in the source container; and
 the controller is further programmed to operate the multi-channel wellplate filling station in the mixing mode in which the liquid mixture is pumped from the source container by the first persitaltic pump through the tubing set and a dispensing head into the wells in a multiwell plate on the repositionable wellplate platform and is also programmed to activate the second peristaltic pump to mix the liquid mixture in the source container.

* * * * *